(12) United States Patent
Prasad

(10) Patent No.: US 11,992,512 B2
(45) Date of Patent: May 28, 2024

(54) COMPOSITION AND METHOD FOR TREATING DYSPEPSIA

(71) Applicant: Kodimule Shyam Prasad, Bangalore (IN)

(72) Inventor: Kodimule Shyam Prasad, Bangalore (IN)

( * ) Notice: Subject to any disclaimer, the term of this patent is extended or adjusted under 35 U.S.C. 154(b) by 0 days.

(21) Appl. No.: 17/728,564

(22) Filed: Apr. 25, 2022

(65) Prior Publication Data
US 2022/0323527 A1 Oct. 13, 2022

Related U.S. Application Data

(62) Division of application No. 16/701,538, filed on Dec. 3, 2019, now Pat. No. 11,338,006.

(60) Provisional application No. 62/775,845, filed on Dec. 5, 2018.

(51) Int. Cl.
A61K 36/28 (2006.01)
A61K 31/357 (2006.01)
A61K 36/23 (2006.01)
A61P 1/14 (2006.01)

(52) U.S. Cl.
CPC ............ *A61K 36/28* (2013.01); *A61K 31/357* (2013.01); *A61K 36/23* (2013.01); *A61P 1/14* (2018.01)

(58) Field of Classification Search
None
See application file for complete search history.

(56) References Cited

PUBLICATIONS

Otillinger et al. (2013) Wien Med. Wochnschr. 163: 65-72. (Year: 2013).*
Mahendra et al. (2012) Pharmacognosy Reviews vol. 6, Issue 12: 141-146. (Year: 2012).*

* cited by examiner

*Primary Examiner* — Russell G Fiebig
(74) *Attorney, Agent, or Firm* — TMB Law; Timothy M. Brown

(57) ABSTRACT

The invention provides a composition and method for treating dyspepsia with *asafoetida* and milk thistle extract. A method of making the inventive composition is contemplated.

10 Claims, 8 Drawing Sheets

COMPOSITION AND METHOD FOR TREATING DYSPEPSIA

CROSS-REFERENCE TO RELATED APPLICATIONS

This application is a divisional of U.S. application Ser. No. 16/701,538 filed Dec. 3, 2019, which claims the benefit of U.S. Provisional Application No. 62/775,845 filed Dec. 5, 2018. The entire contents of these applications are incorporated herein by reference for all purposes.

FIELD OF THE INVENTION

The invention relates to treatments for dyspepsia. More particularly, the invention relates to a composition comprising *asafoetida* and milk thistle extract and methods of making and using the same in treating dyspepsia.

BACKGROUND OF THE INVENTION

There is accumulating evidence that distinct subgroups of uninvestigated dyspepsia exist in the general population, suggesting that separate evaluation and treatment strategies might be needed (Aro et al. 2009; Choung et al. 2007). The contributing factors for the pathophysiology of functional dyspepsia (FD) such as gastrointestinal dysmotility, inflammation of gastric mucosa, delayed gastric emptying, and *Helicobacter pylori* infection, have been investigated previously. However, conventional treatment options have been proven to be of limited efficacy in patients with FD. For example, some of the current strategies such as prokinetic drug treatment have been clinically proven to relieve the symptoms of FD only in a small portion of patients (Tally, 1999). Many FD patients seek herbal remedies as alternative medication because of the limitations of conventional FD treatments (Lahner et al. 2013).

A number of medicinal plant preparations have been implicated in the treatment of FD. Several combinations of traditional herbs have been reported as effective in the treatment of FD (Monkemuller and Malfertheiner, 2006). Owing to the advantages of plant-based drugs in healthcare management, such as minimal side effects and lesser toxicity, much attention has been given to medicinal plants for treating FD.

*Ferula asafoetida*, belonging to the family Umbelliferae, is a perennial plant native to central Asia, particularly Afghanistan, Iraq, and Iran. It is also widely distributed in Europe and North Africa (Sahebkar and Iranshahi, 2010). *Asafoetida* is the oleo-gum-resin (exudates obtained from the rhizome) of *F. asafoetida* (Duan et al. 2002). *Asafoetida* is called Hing or Hingu in India. *Asafoetida* is valued in the Indian cuisine as a flavouring agent due to its characteristic odor.

*Silybum marianum* (Fam. Asteriaceae) is a medicinal plant valued for its potential health benefits. Originally, *S. marianum* was a native of Asia and Southern Europe, but is now found throughout the world (Sewell and Rafieiankopaei, 2014). *S. marianum* is commonly known by several names which includes milk thistle, Marian thistle, Mary's thistle, Saint Mary's thistle and scotch thistle (Simanek et al. 2000). *S. marianum* has shiny pale green leaves and red to purple flowers with white veins. Experimental and clinical evidence suggest that the plant is used extensively for treating liver disorders due to its potential antioxidant and hepatoprotective effects (Natural Medicines Comprehensive Database, 2012). It has also been studied for hypoglycemic and antidiabetic activities (Khazim et al. 2013).

SUMMARY OF THE INVENTION

The inventor surprisingly discovered that combining *asafoetida* and milk thistle extract provides a synergistic effect in the treatment of dyspepsia.

It is therefore an object of the invention to provide a composition comprising *asafoetida* and milk thistle extract. In some aspects, the composition comprises *asafoetida* and milk thistle extract in a ratio of 1:3.

A further object of the invention is to provide a method of treating dyspepsia, comprising administering to a patient in need thereof *asafoetida* and milk thistle extract.

In some aspects, the *asafoetida* and milk thistle extract are administered simultaneously, while in other aspects the *asafoetida* and milk thistle extract are administered sequentially.

In some aspects, the administering step comprises administering a composition comprising *asafoetida* and milk thistle extract.

In some aspects, the administering step comprises administering a composition comprising *asafoetida* and milk thistle extract in a ratio of about 1:3.

These and other objects of the invention will become clear to one skilled in the art in view of the accompanying drawings and description which disclose some, but not necessarily all, of the embodiments of the invention.

Definitions

Figure 1:
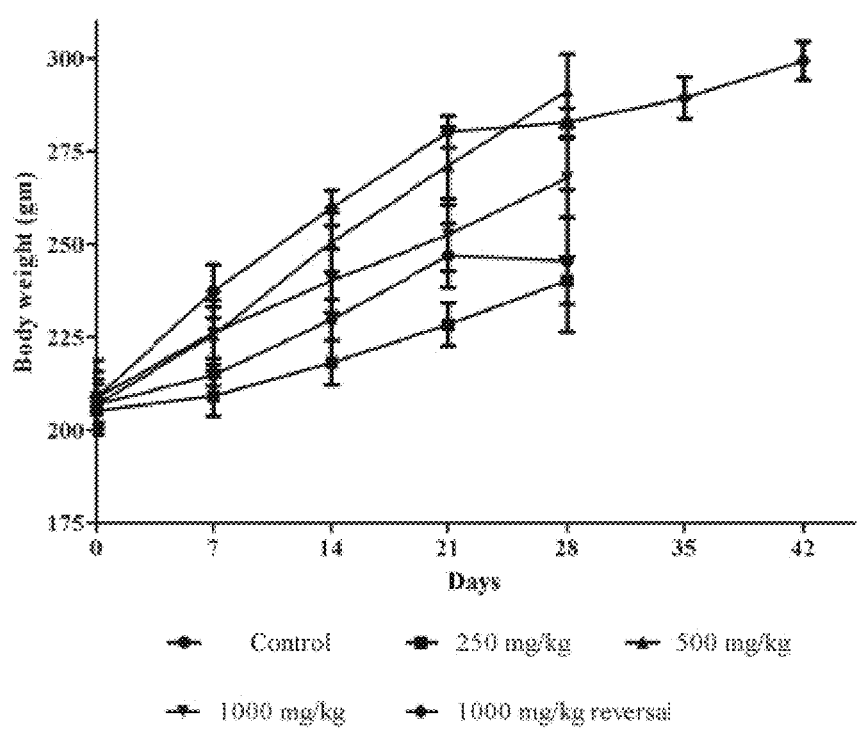
FIG. 1. shows the effect of 28-day treatment on body weight of male rats. Values are expressed as mean±SEM (n=5). *$p<0.05$ were considered significant using one-way ANOVA followed by Tukey's multiple comparison tests.
Figure 2:
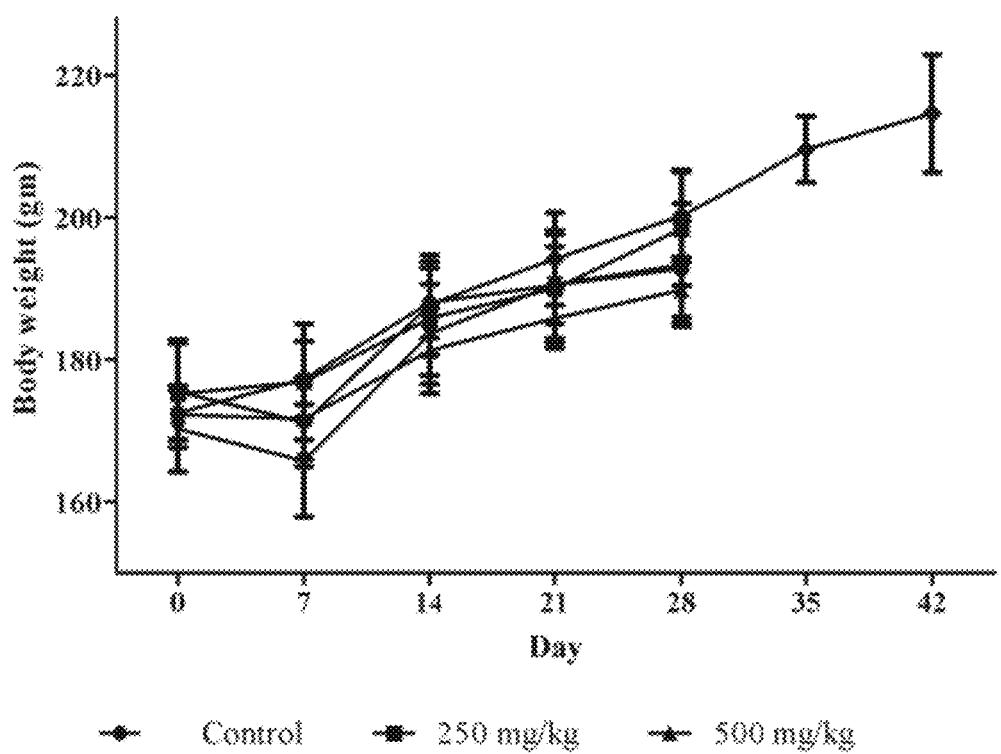
FIG. 2 shows the effect of 28-day treatment on body weight of female rats. Values are expressed as mean±SEM (n=5). *$p<0.05$ were considered significant using one way ANOVA followed by Tukey's multiple comparison tests.
Figure 3:
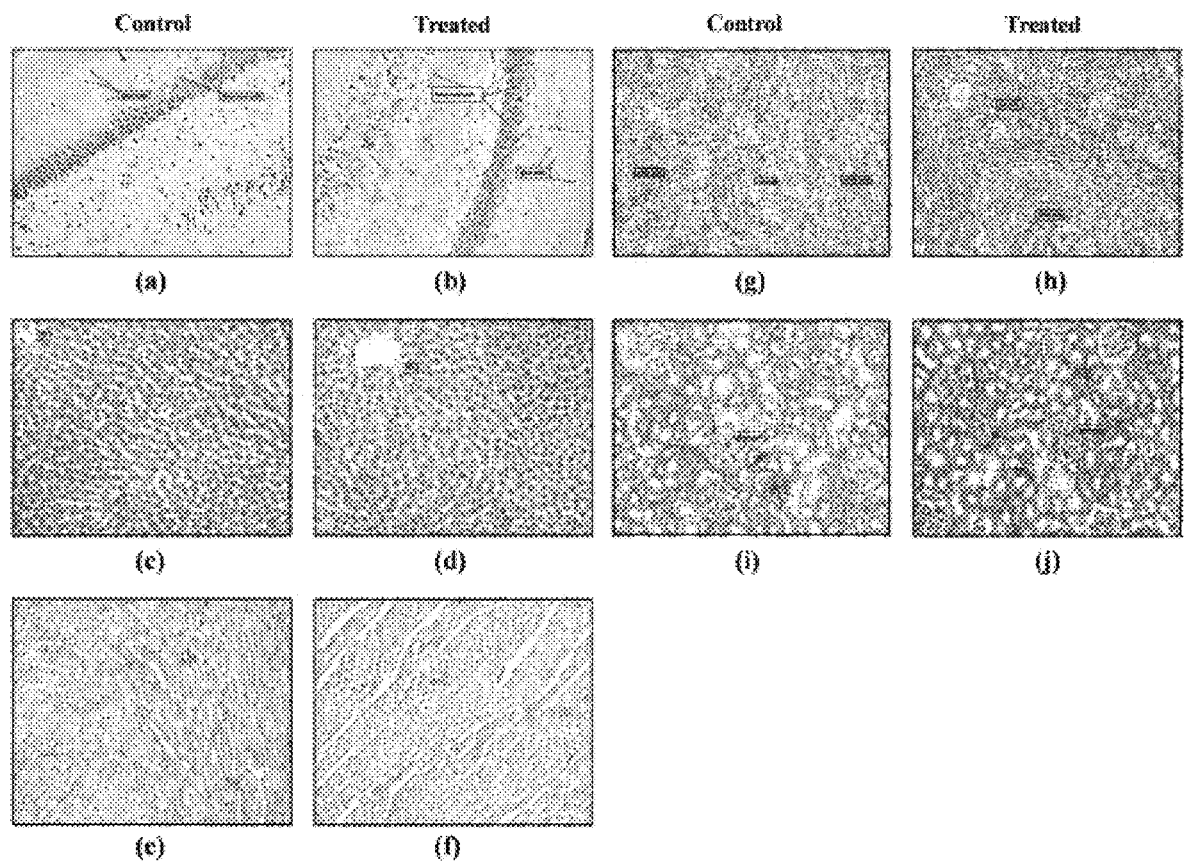
FIG. 3 shows the effect of 1000 mg $kg^{-1}$ on histology of vital organs of male rats. (a) and (b): brain; (c) and (d): liver; (e) and (f): heart; (g) and (h): spleen; (i) and (j): kidney. cv, central vein; DCT, distal convoluted tubule; PCT, proximal convoluted tubule.
Figure 4:
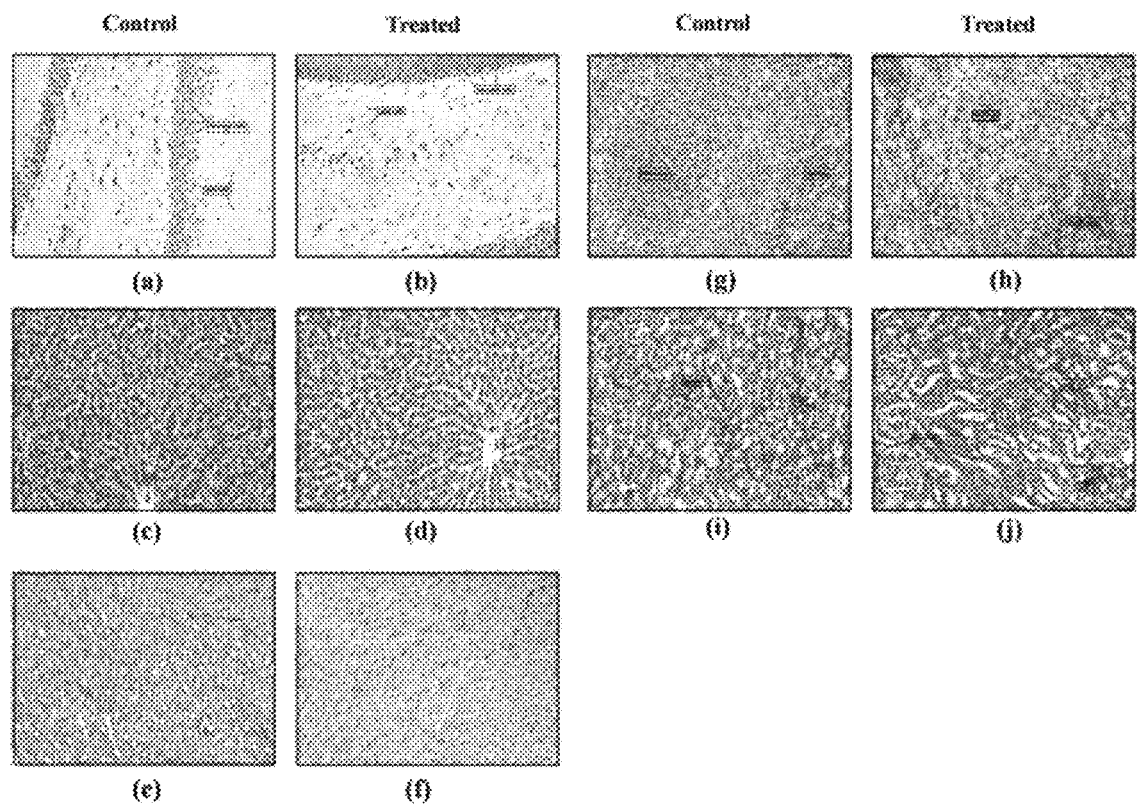
FIG. 4 shows the effect of 1000 mg $kg^{-1}$ on histology of vital organs of female rats. (a) and (b): brain; (c) and (d): liver; (e) and (f): heart; (g) and (h): spleen; (i) and (j): kidney. cv, central vein; DCT, distal convoluted tubule; PCT, proximal convoluted tubule.
Figure 5A:
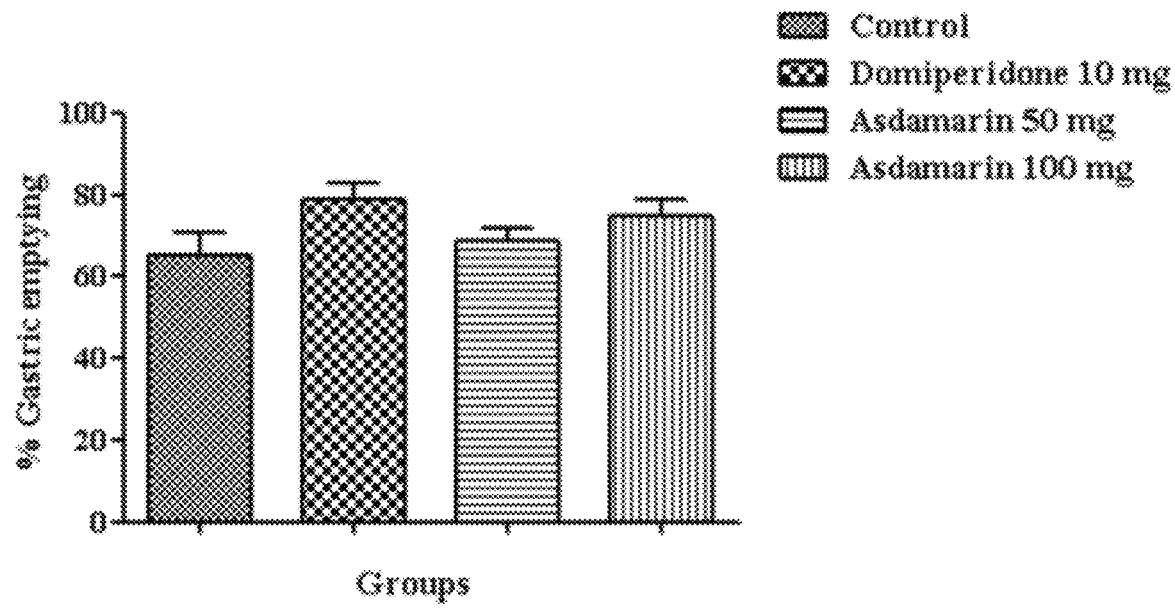
FIG. 5A shows the effect on gastric emptying in Sprague Dawley rats. Values are expressed as mean±SEM (n=6). Data were analyzed by one way ANOVA followed by Dunnet's t test. ***$p<0.001$ compared to control group.
Figure 5B:
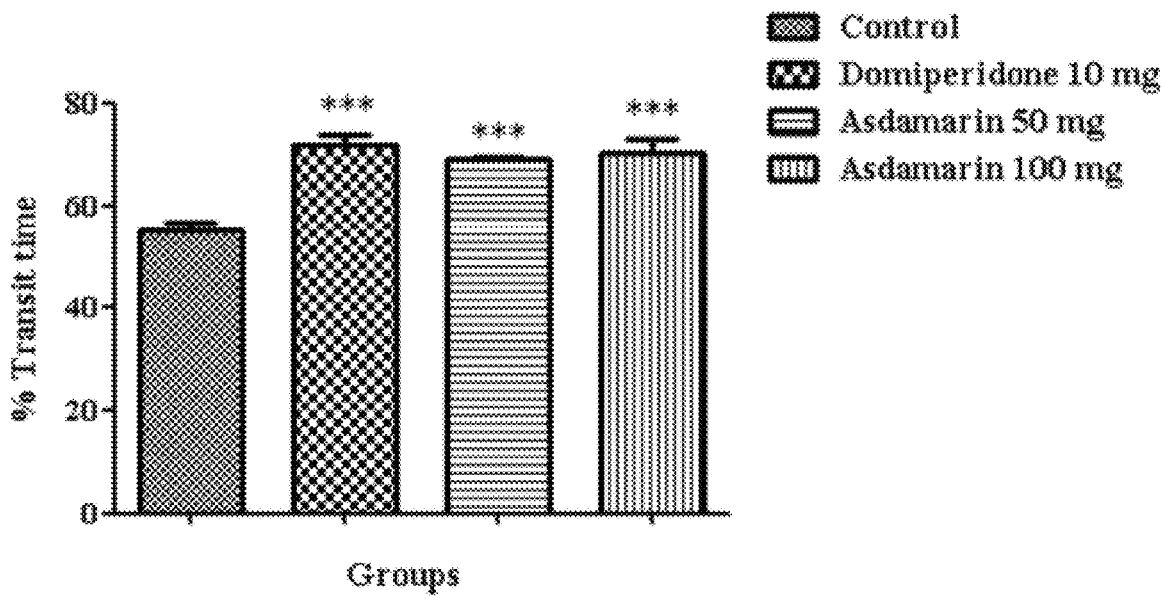
FIG. 5B shows the effect on percentage intestinal transit time in Sprague Dawley rats. Values are expressed as mean±SEM (n=6). Data were analyzed by one way ANOVA followed by Dunnet's t test. ***$p<0.001$ compared to control group.
Figure 6:
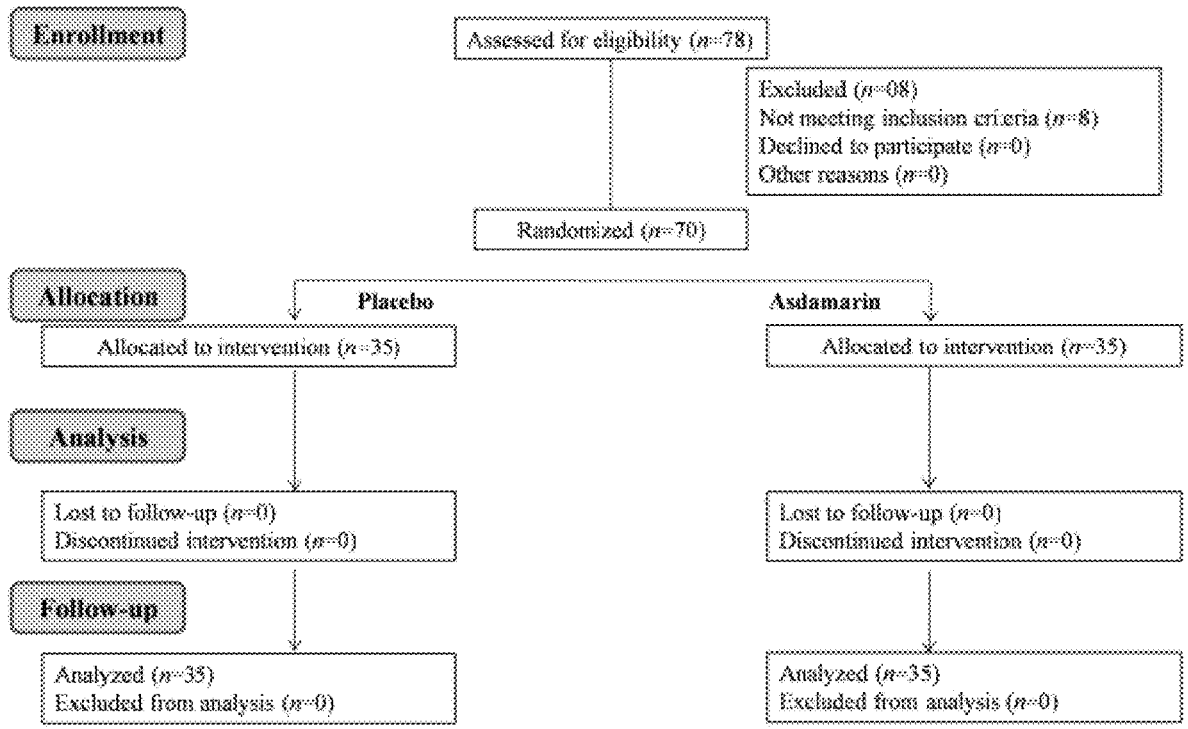
FIG. 6 is a flow chart for subject participation.
Figure 7:
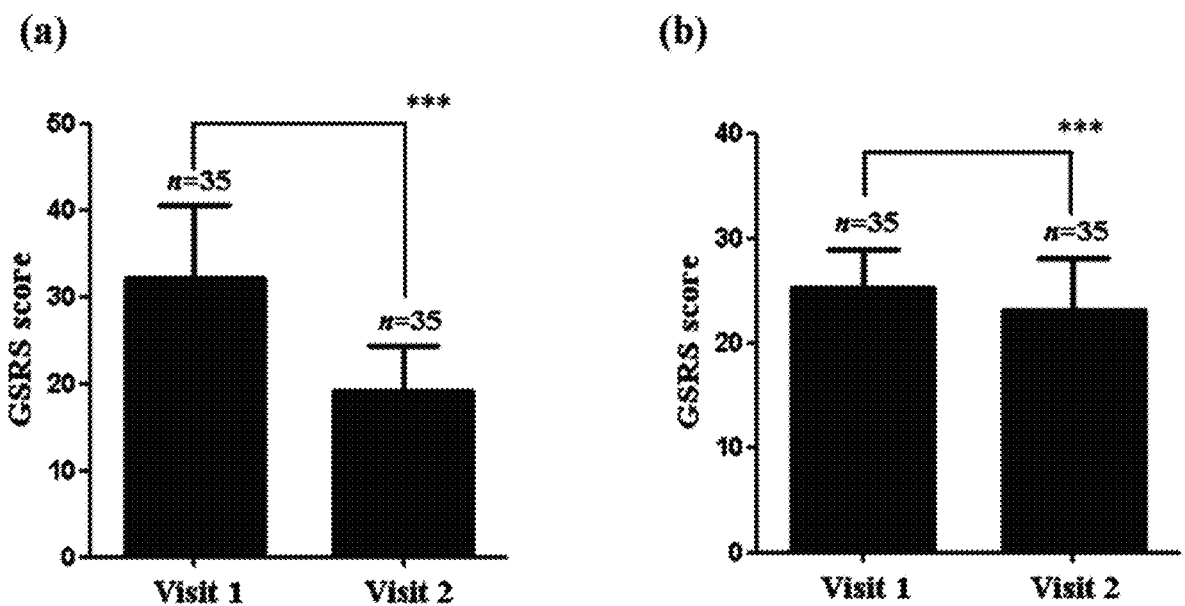
FIG. 7 is a summary score for symptom severity on the Gastrointestinal Symptom Rating Scale (GSRS) of (a) composition and (b) placebo treatment groups from baseline (Visit 1) to visit 2 (after 7 days treatment). Values are mean±SD. Data were analyzed by paired t-test. ***$p<0.001$ compared to baseline.
Figure 8:
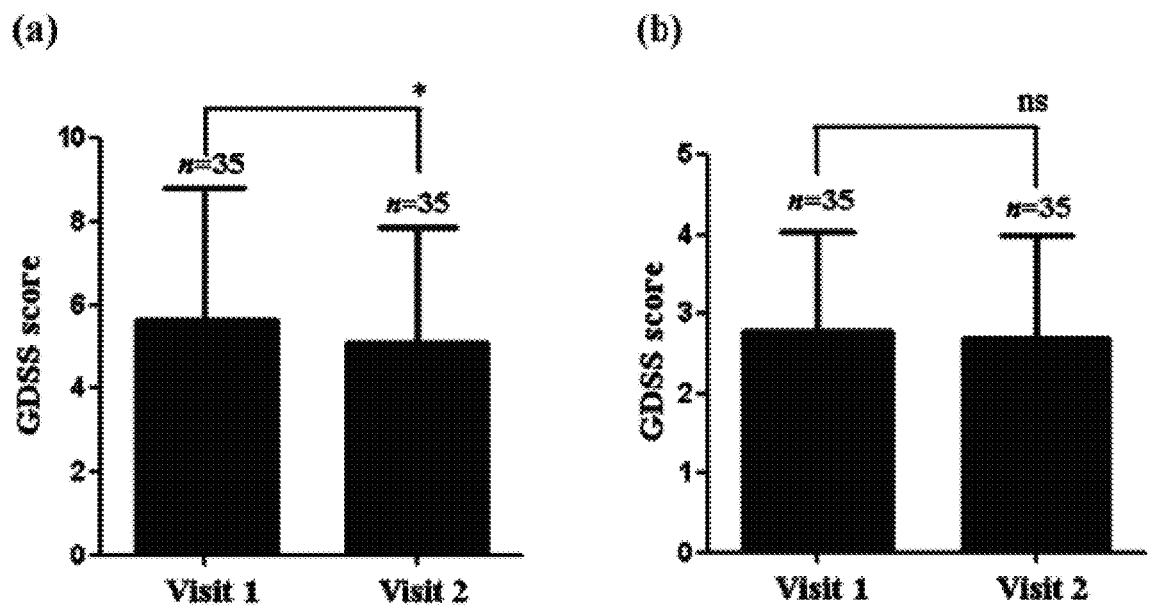
FIG. 8 is a summary score for symptom severity on the Glasgow Dyspepsia Severity Score (GDSS) of (a) composition and (b) placebo treatment groups from baseline (Visit 1) to visit 2 (after 7 days treatment). Values are mean±SD. Data were analyzed by paired t-test. *$p<0.05$ compared to baseline. ns, not significant.
Figure 9:
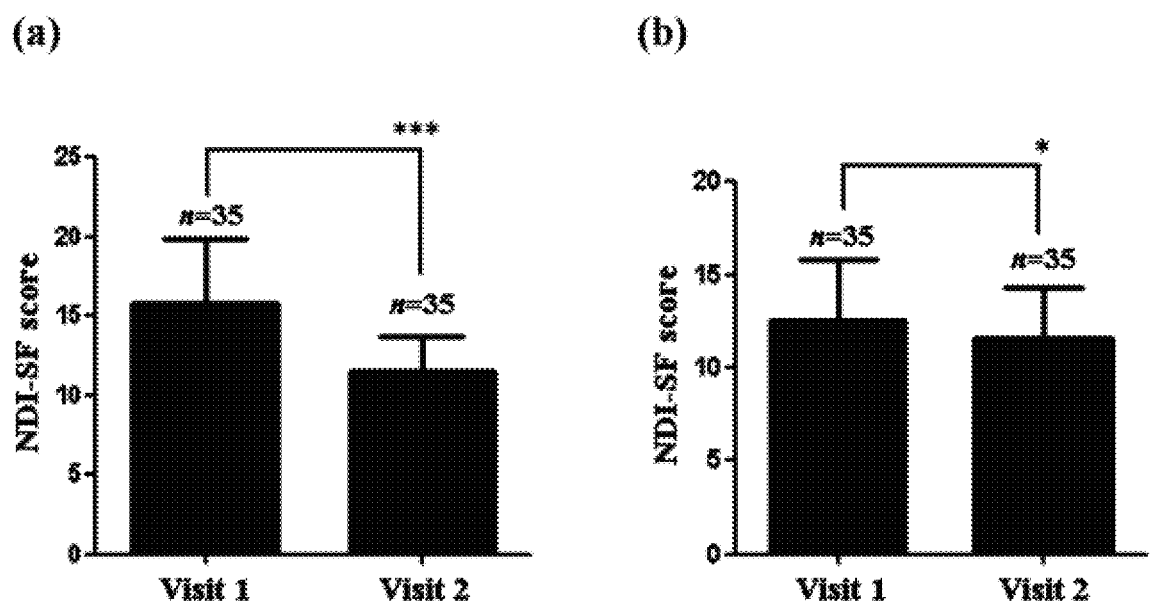
FIG. 9 is a summary score for symptom severity on the Nepean Dyspepsia Index (NDI-SF) of (a) composition and (b) placebo treatment groups from baseline (Visit 1) to visit 2 (after 7 days treatment). Values are mean±SD. Data were analyzed by paired t-test. *$p<0.05$ and ***$p<0.001$ compared to baseline.
Figure 10:
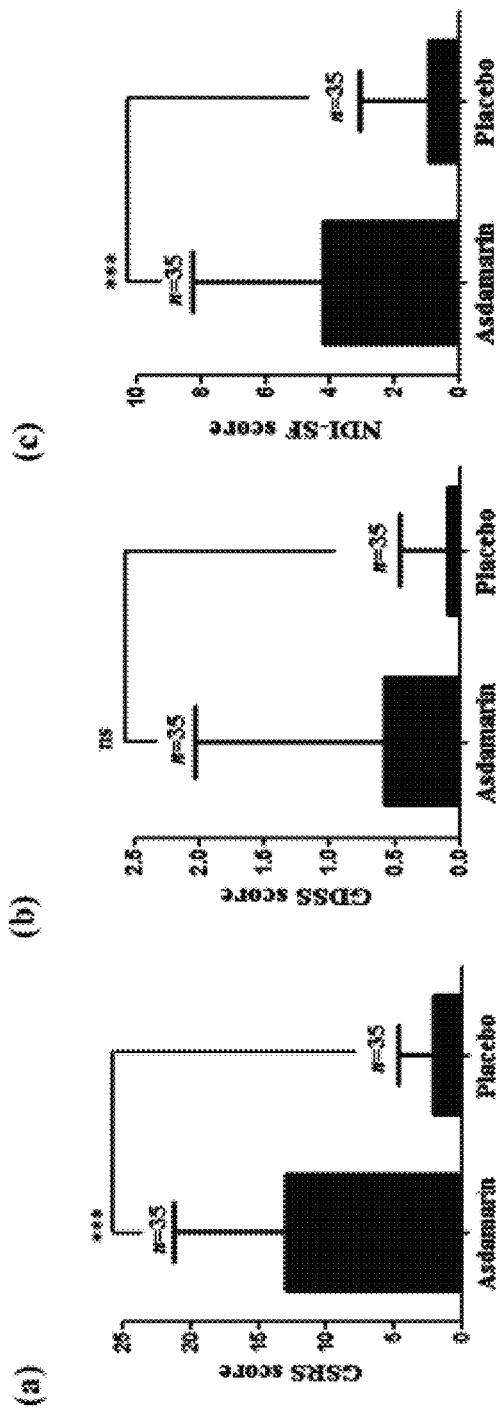
FIG. 10 shows changes from baseline in the summary score for symptom severity on the Gastrointestinal Symptom Rating Scale (GSRS), Glasgow Dyspepsia Severity Score (GDSS) and Nepean Dyspepsia Index (NDI-SF). Values are mean±SD. Data were analyzed by independent t-test. ***$p<0.001$ compared to placebo group. ns, not significant.

As used herein, the term "*asafoetida*" refers to an extract or exudate from the rhizome or tap root of herbs of the genus *Ferula*, including without limitation *Ferula asafoetida*. *Asafoetida* can comprise, without limitation, gum oleoresin.

"*Silibum marianum* extract," "*S. marianum* extract," and "milk thistle extract" are used interchangeably herein to refer to an extract from the plant *Silibum marianum*.

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% to the referenced quantity, level, value, number, frequency, percentage, dimension, size, amount, weight or length.

The term "patient" as used herein to refers to mammals, including, without limitation, humans and non-human primates, as well as livestock and companion and laboratory research animals. The term can refer to any of the foregoing that have been diagnosed with dyspepsia, are experiencing dyspepsia, are currently following a therapeutic regimen for dyspepsia, or are at risk of developing dyspepsia.

The term "dyspepsia" as used herein refers to a condition characterized by an impairment of the power or function of digestion that can arise as a symptom of a primary gastrointestinal dysfunction or as a complication due to other disorders such as, for example, appendicitis, gallbladder disturbances, ulcers, gastroesophageal reflux disease, or malnutrition.

The phrases "treating dyspepsia," "treatment of dyspepsia," "treatment of dyspepsia," and the like are used herein to refer relieving, preventing, or easing one or more symptoms associated with or resulting from dyspepsia.

DETAILED DESCRIPTION

The invention generally relates to the treatment of dyspepsia. More particularly, the invention relates to the treatment of dyspepsia with a combination of *asafoetida* and milk thistle extract.

In at least one aspect, the invention provides a composition comprising *asafoetida* and milk thistle extract. *Asafoetida* for formulating the composition can be obtained from the rhizomes of any herb belonging to the genus *Ferula*, including without limitation *Ferula asafoetida*. In at least one non-limiting embodiment, the *asafoetida* is an exudate or extract of the rhizomes of an herb from the genus *Ferula*. The *asafoetida* can be an exudate or extract of the rhizomes of *Ferula asafoetida*. The *asafoetida* can comprise oleoresin. The *asafoetida* can consist of, or consist essentially of, oleoresin. The oleoresin can be gum oleoresin.

Milk thistle extract for the composition can be obtained from any part of the plant *Silibum marianum* that is capable of providing an extract capable of treating dyspepsia as disclosed herein. Portions of the plant for making the milk thistle extract include, but are not limited to, leaves, seeds, flowers, stems, stalks, roots, buds, seeds, or combinations thereof. The extract can be obtained by subjecting one or more of such plant parts to extrusion or solvent extraction. Suitable solvents for obtaining the milk thistle extract include, but are not limited to, aqueous solvents, alcohol-based solvents, supercritical fluids, polar organic solvents, such as acetone and methylethyl ketone, or combinations thereof, for example. Non-limiting examples of alcohol-based solvents include, but are not limited to, ethanol, isopropyl alcohol, methanol, and combinations thereof. The supercritical fluid can be, but is not necessarily limited to, carbon dioxide. The extract can be a whole plant extract wherein no other components from the extract are removed after extrusion or extraction.

In at least one aspect of the invention, the milk thistle extract comprises silymarin. The milk thistle can be standardized for silymarin. In one non-limiting embodiment, the milk thistle extract is standardized to contain at least about 25% silymarin, at least about 30% silymarin, at least about 35% silymarin, at least about 40% silymarin, at least about 45% silymarin, or at least about 50% silymarin. The milk thistle extract can be standardized to contain between about 25% to about 30% silymarin, about 25% to about 35% silymarin, about 25% to about 40% silymarin about 25% to about 45% silymarin, or about 25% to about 50% silymarin.

The composition can be formulated to comprise *asafoetida* and milk thistle extract in a selected ratio. The ratio can be any ratio that is capable of treating dyspepsia as disclosed herein. In one non-limiting embodiment, the composition comprises *asafoetida* and milk thistle extract in a ratio of about 1:3, respectively. The composition can comprise *asafoetida* and milk thistle extract in a ratio of about 1:3, wherein the milk thistle extract is standardized to contain at least about 25% silymarin.

The composition can take any administration form capable of treating dyspepsia as disclosed herein. The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, beadlet, gummy, gel, sol, injection, and combinations thereof. The composition can be formulated for oral administration. The composition can be combine with a vitamin, mineral, extract, essential oil, amino acid, protein, carbohydrate, lipid, fatty acid, food, beverage, nutritional or dietary supplement, excipient, pharmaceutically acceptable carrier, bulking agent, binding agent, caffeine, flavoring, sweetener, preservative, or combinations thereof. In at least one aspect of the invention, the composition is provided in bulk. The composition can be provided in bulk for the manufacture of foods, nutritional supplements, nutraceuticals, dietary supplements and/or food supplements for the treatment of pain. Bulk quantities of the composition can be packaged, stored and/or distributed in drums, bags, boxes, containers and the like. Such containers can be configured to prevent or inhibit the oxidation of the active ingredients of the composition, such as oxidation resulting from exposure to air.

In at least one embodiment, the composition can employ controlled, sustained, or extended release formulations known collectively as "modified release" formulations. For use with the methods disclosed herein, the composition can be administered by modified release systems or by delivery devices known by those of ordinary skill in the art. Non-limiting examples of modified release and delivery systems include, but are not limited to, those described in the following U.S. Patents, the entire disclosures of which are incorporated herein by reference for all purposes: U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Dosage forms for the composition can employ one or more modifying release ingredients. Suitable modified release ingredients include, without limitation, hydropropylmethyl cellulose, other polymer matrices, gels, permeable membranes, osmotic systems, multilayer coatings, microparticles, liposomes, microspheres, and combinations thereof.

In at least one aspect, the invention provides a method of treating dyspepsia. In one non-limiting embodiment, the method is practiced by administering to a patient in need thereof a composition as disclosed herein. In other embodiments, *asafoetida* and milk thistle extract are administered separately, either simultaneously or in sequence. For example, a composition comprising *asafoetida* can be administered to the patient, followed by administering a composition comprising milk thistle extract. In some embodiments, these steps of administration are reversed. The extracts can be administered in sequence in a selected ratio. For example, the extracts can be administered to a patient in amounts that result in an *asafoetida* to milk thistle extract ratio of about 1:3. Milk thistle extract that is administered separately can be standardized to contain silymarin according to the amounts disclosed herein.

The composition can be administered systemically and/or locally. Suitable administration routes for the composition include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parenteral, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. The composition can be administered by irrigation, drip, infusion, or topically by a dressing, patch, or bandage that is in contact with the composition.

In at least one aspect, the composition is administered to a patient in need of treatment for dyspepsia. The patient can be experiencing dyspepsia, at risk of developing dyspepsia, or currently receiving an alternate treatment for dyspepsia. The dyspepsia can be the result of one or more underlying diseases or disorders, including, without limitation: gastritis; duodenal inflammation; peptic ulcer disease affecting one or more of the stomach, esophagus, and duodenum, including peptic ulcer disease resulting from *H. pylori*; intestinal blockage; hiatus hernia; medication side effects; excess alcohol intake; food allergies; smoking; acid reflux disease; gastric cancer; thyroid disease; pancreatitis; pregnancy; irritable bowel syndrome; gastroparesis; food poisoning; bacterial infection; viral infection; and pancreatic or bile duct abnormalities. The dyspepsia can be functional dyspepsia in which the underlying cause of the dyspepsia is unknown. The dyspepsia can be non-ulcer functional dyspepsia.

Administering the composition can treat one or more symptoms associated with dyspepsia, including, without limitation, stomach pain, abdominal pain, bloating, heartburn, nausea, vomiting, feeling full or satiated with little or no eating, belching, flatulence, burning in the stomach and abdomen, stomach growling, acidic taste, gastrointestinal dysmotility, delayed gastric emptying, and gastrointestinal gas. Administering the composition can reduce, arrest, prevent, or alleviate one or more symptoms of dyspepsia.

The composition can be administered in any dose effective in the treatment of dyspepsia. The composition can be administered at a dose of between about 100 mg/day and about 1,000 mg/day. The composition can be administered at a dose of about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, about 500 mg/day, about 525 mg/day, about 550 mg/day, about 575 mg/day, about 600 mg/day, about 700 mg/day, about 800 mg/day, about 900 mg/day, or about 1,000 mg/day.

The dose of the composition can be determined by body weight. The composition can be administered at a dose of between about 50 mg/kg body weight and about 2,000 mg/kg body weight. The composition can be administered in a dose of about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, or about 250 mg/kg body weight. The composition can be administered one or more times per day, per week, or per month. One skilled in the art will appreciate that the dose and administration schedule may be adjusted based on one or more of the severity of the patient's symptoms, the desired therapeutic effect, and the patient's response to treatment.

In at least one aspect, the invention provides a method for making the composition disclosed herein. The composition can be made by combining *asafoetida* and milk thistle extract. The extracts can be combined by at least one of mixing, folding, stirring, shaking, and blending. The milk thistle extract can be standardized for silymarin as disclosed herein.

Example 1—Toxicity Assessment the Composition

A composition of *asafoetida* and milk thistle extract in a ratio of 1:3 in beadlet form was evaluated for potential acute and sub-acute oral toxicity in Wistar rats.

A single dose acute oral toxicity of the composition was evaluated at 2,000 mg/kg body weight in female Wistar rats.

Following a 14-day observation it was evident that treatment with the composition did not induce any abnormal body weight changes, toxic clinical signs, mortality, or behavioural changes in rats. From these observations, it was concluded that LD50 of the composition was more than 2,000 mg/kg body weight in rats.

The repeated dose sub-acute oral toxicity of the composition was evaluated at 250, 500 and 1,000 mg/kg body weight in male and female Wistar rats. The composition did not significantly alter feed or water consumption (Tables 1 & 2) and did not affect a body weight change in rats compared to the control group.

TABLE 1

Effect of the composition on mean feed consumption (g) in rats

| Sex | Day | Control | 250 mg/kg | 500 mg/kg | 1,000 mg/kg | 1,000 mg/kg reversal |
|---|---|---|---|---|---|---|
| Male | 7 | 28.46 ± 0.94 | 27.49 ± 0.99 | 35.71 ± 1.08 | 30.8 ± 1.15 | 36.63 ± 1.81 |
|  | 14 | 34.46 ± 1.35 | 32.46 ± 3.27 | 39.54 ± 2.68 | 36.51 ± 0.96 | 38.57 ± 2.43 |
|  | 21 | 35.46 ± 2.50 | 30.57 ± 1.10 | 44.74 ± 0.65 | 41.69 ± 1.53 | 39.06 ± 1.14 |
|  | 28 | 30.69 ± 1.46 | 32.74 ± 1.49 | 30.14 ± 0.55 | 42.8 ± 1.72 | 38.66 ± 1.79 |
|  | 35 | — | — | — | — | 37.09 ± 2.27 |
|  | 42 | — | — | — | — | 36.94 ± 1.05 |
| Female | 7 | 30.51 ± 1.14 | 25.77 ± 1.19 | 26.46 ± 2.84 | 29.29 ± 1.31 | 27.63 ± 3.13 |
|  | 14 | 29.6 ± 29.69 | 24.4 ± 28.03 | 28.8 ± 30.11 | 33.2 ± 35.54 | 28.00 ± 29.09 |
|  | 21 | 32.00 ± 29.89 | 27.00 ± 24.17 | 27.6 ± 25.60 | 35.00 ± 34.17 | 36.2 ± 30.14 |
|  | 28 | 32.83 ± 2.83 | 36.8 ± 2.43 | 35.94 ± 1.91 | 38.26 ± 2.20 | 37.11 ± 2.06 |
|  | 35 | — | — | — | — | 40.31 ± 3.37 |
|  | 42 | — | — | — | — | 27.17 ± 2.13 |

Values are expressed as mean ± SEM (n = 5 male and 5 female rats for each group). Data were analyzed by one-way ANOVA followed by multiple comparison test.
*$p < 0.05$ compared to control group.
R: Reversal group.

TABLE 2

Effect of the composition on average water consumption (mL) in rats

| Sex | Day | Control | 250 mg/kg | 500 mg/kg | 1,000 mg/kg | 1,000 mg/kg reversal |
|---|---|---|---|---|---|---|
| Male | 7 | 17.83 ± 0.95 | 16.8 ± 0.42 | 18.31 ± 0.7 | 18.19 ± 0.61 | 21.7 ± 0.86 |
|  | 14 | 18.8 ± 0.36 | 17.72 ± 0.93 | 22.13 ± 0.7 | 20.12 ± 0.58 | 24.36 ± 0.47 |
|  | 21 | 20.84 ± 0.46 | 19.3 ± 0.24 | 24.64 ± 0.57 | 21.44 ± 0.72 | 23.92 ± 0.14 |
|  | 28 | 21.54 ± 1.03 | 20.09 ± 0.47 | 24.03 ± 0.54 | 22.81 ± 0.69 | 23.3 ± 0.66 |
|  | 35 | — | — | — | — | 19.78 ± 0.29 |
|  | 42 | — | — | — | — | 23.95 ± 0.35 |
| Female | 7 | 14.62 ± 0.30 | 14.18 ± 0.46 | 13.86 ± 0.35 | 12.61 ± 0.90 | 14.00 ± 0.82 |
|  | 14 | 15.83 ± 0.57 | 16.43 ± 0.48 | 15.15 ± 0.33 | 17.17 ± 0.34 | 16.90 ± 1.27 |
|  | 21 | 15.77 ± 0.87 | 15.81 ± 0.33 | 15.11 ± 0.54 | 17.12 ± 0.30 | 17.63 ± 0.28 |
|  | 28 | 16.35 ± 0.68 | 17.74 ± 0.68 | 17.22 ± 0.39 | 18.89 ± 0.52 | 19.63 ± 1.11 |
|  | 35 | — | — | — | — | 20.69 ± 0.49 |
|  | 42 | — | — | — | — | 18.88 ± 1.08 |

Values are expressed as mean ± SEM (n = 5 male and 5 female rats for each group). Data were analyzed by one-way ANOVA followed by Tukey's multiple comparison test.
*$p < 0.05$ compared to control group.
R: Reversal group.

Relative organ weights of 28-day treated rats were not significantly different from the control animals (Table 3).

TABLE 3

Relative organ weights of rats treated with the composition for 28 days

| | | | Composition (mg/kg, B.W) | | | |
|---|---|---|---|---|---|---|
| Sex | Organ | Control | 250 | 500 | 1,000 | 1,000 Reversal |
| Male | Brain | 0.808 ± 0.05 | 0.795 ± 0.03 | 0.759 ± 0.006 | 0.714 ± 0.042 | 0.686 ± 0.014 |
|  | Heart | 0.368 ± 0.03 | 0.337 ± 0.01 | 0.308 ± 0.006 | 0.326 ± 0.016 | 0.303 ± 0.004 |
|  | Liver | 3.613 ± 0.14 | 3.360 ± 0.13 | 3.511 ± 0.126 | 3.815 ± 0.126 | 2.456 ± 0.047 |
|  | Spleen | 0.486 ± 0.09 | 0.44 ± 0.02 | 0.399 ± 0.036 | 0.447 ± 0.04 | 0.392 ± 0.03 |
|  | Kidneys | 0.339 ± 0.01 | 0.335 ± 0.02 | 0.308 ± 0.019 | 0.341 ± 0.015 | 0.284 ± 0.009 |

TABLE 3-continued

Relative organ weights of rats treated with the composition for 28 days

| Sex | Organ | Control | Composition (mg/kg, B.W) | | | |
|---|---|---|---|---|---|---|
| | | | 250 | 500 | 1,000 | 1,000 Reversal |
| Female | Brain | 0.930 ± 0.033 | 0.858 ± 0.022 | 0.914 ± 0.028 | 0.913 ± 0.019 | 0.874 ± 0.032 |
| | Heart | 0.403 ± 0.026 | 0.388 ± 0.021 | 0.385 ± 0.0187 | 0.396 ± 0.007 | 0.336 ± 0.013 |
| | Liver | 3.349 ± 0.331 | 3.199 ± 0.150 | 3.054 ± 0.228 | 3.150 ± 0.089 | 2.627 ± 0.084 |
| | Spleen | 0.520 ± 0.061 | 0.465 ± 0.076 | 0.448 ± 0.036 | 0.523 ± 0.045 | 0.325 ± 0.026 |
| | Kidneys | 0.503 ± 0.025 | 0.515 ± 0.015 | 0.505 ± 0.022 | 0.521 ± 0.008 | 0.455 ± 0.024 |

Values are expressed as mean ± SEM (n = 10 for each group).
*$p < 0.05$ were considered significant using one-way ANOVA followed by Tukey's multiple comparison test.
*denote significant difference compared to control.
R: Reversal group.

The effect of 28-day treatment with the composition on hematological parameters is presented in Table 4. Except for the marginal changes in some of the parameters, the hematological assessment showed no significant change in the treatment groups as compared to the control group. Further, composition administration exerted no significant changes in the biochemical analyses such as renal (urea and creatinine) and liver function (alanine aminotransferase, aspartate aminotransferase and alkaline phosphatase) parameters, total protein and albumin (Table 5).

TABLE 4

Effect of the composition on hematological parameters in rats

| | Unit | Control | Composition (mg/kg, B.W) | | | |
|---|---|---|---|---|---|---|
| | | | 250 | 500 | 1,000 | 1,000 Reversal |
| Male | | | | | | |
| Hemoglobin | g/dL | 16.78 ± 0.56 | 17.60 ± 0.27 | 15.40 ± 0.66 | 16.06 ± 0.56 | 16.26 ± 0.51 |
| RBC | $10^6$/μL | 9.848 ± 1.25 | 8.55 ± 0.15 | 7.72 ± 0.24 | 7.97 ± 0.3 | 7.97 ± 0.27 |
| HCT | % | 43.98 ± 0.66 | 45.66 ± 0.53 | 40.40 ± 1.08 | 41.24 ± 1.84 | 41.00 ± 1.26 |
| MCV | fL | 51.98 ± 1.03 | 53.54 ± 1.16 | 52.48 ± 1.33 | 51.80 ± 0.85 | 51.52 ± 0.82 |
| MCH | Pg | 19.74 ± 0.39 | 20.56 ± 0.41 | 19.86 ± 0.3 | 20.12 ± 0.20 | 20.34 ± 0.32 |
| MCHC | g/dL | 38.10 ± 1.06 | 38.50 ± 0.22 | 38.04 ± 1.06 | 38.96 ± 0.43 | 39.60 ± 0.35 |
| Platelets | $10^3$/μL | 270.6 ± 21.78 | 307.4 ± 16.85 | 313.0 ± 16.88 | 313.6 ± 10.16 | 311.4 ± 20.48 |
| WBC | $10^3$/μL | 22.06 ± 0.87 | 19.22 ± 3.12 | 19.46 ± 1.29 | 19.62 ± 2.76 | 20.04 ± 2.11 |
| Lymphocytes | % | 90.92 ± 1.66 | 88.74 ± 0.88 | 93.84 ± 0.62 | 93.94 ± 0.76 | 90.20 ± 1.47 |
| Monocytes | % | 3.18 ± 0.41 | 3.42 ± 0.19 | 2.35 ± 0.16 | 2.27 ± 0.14 | 2.97 ± 0.30 |
| Neutrophils | % | 4.54 ± 1.08 | 6.38 ± 0.7 | 2.80 ± 0.41 | 2.82 ± 0.56 | 5.56 ± 1.08 |
| Eosinophils | % | 1.33 ± 0.17 | 1.43 ± 0.07 | 0.99 ± 0.07 | 0.95 ± 0.06 | 1.25 ± 0.12 |
| Basophils | % | 0.06 ± 0.02 | 0.06 ± 0.02 | 0.06 ± 0.02 | 0.06 ± 0.02 | 0.06 ± 0.02 |
| Clotting time | Seconds | 33.0 ± 14.59 | 32.60 ± 4.49 | 39.80 ± 21.67 | 25.00 ± 4.50 | 27.40 ± 5.97 |
| Female | | | | | | |
| Hemoglobin | g/dL | 16.68 ± 0.57 | 15.48 ± 0.30 | 16.64 ± 0.466 | 15.50 ± 0.59 | 15.42 ± 0.34 |
| RBC | $10^6$/μL | 7.57 ± 0.26 | 7.67 ± 0.21 | 7.13 ± 0.24 | 6.93 ± 0.62 | 7.45 ± 0.10 |
| HCT | % | 43.98 ± 1.66 | 39.22 ± 0.53 | 38.78 ± 1.03 | 36.84 ± 3.15 | 39.36 ± 0.72 |
| MCV | fL | 58.14 ± 1.22 | 54.28 ± 1.18 | 56.74 ± 0.83 | 60.32 ± 1.09 | 56.90 ± 0.33 |
| MCH | Pg | 22.00 ± 0.29 | 20.16 ± 0.39 | 20.48 ± 0.31 | 21.38 ± 1.59 | 20.64 ± 0.27 |
| MCHC | g/dL | 37.90 ± 0.36 | 39.42 ± 0.26 | 39.74 ± 0.31 | 40.18 ± 2.81 | 39.14 ± 0.35 |
| Platelets | $10^3$/μL | 310.8 ± 40.08 | 345.2 ± 12.87 | 300.0 ± 28.68 | 338.8 ± 41.25 | 272.8 ± 18.13 |
| WBC | $10^3$/μL | 11.02 ± 1.71 | 8.28 ± 1.25 | 8.40 ± 1.38 | 9.36 ± 1.53 | 9.36 ± 1.58 |
| Lymphocytes | % | 91.28 ± 1.66 | 94.30 ± 0.24 | 94.64 ± 0.79 | 93.04 ± 0.58 | 92.18 ± 1.82 |
| Monocytes | % | 2.954 ± 0.52 | 2.18 ± 0.11 | 2.19 ± 0.34 | 2.016 ± 0.24 | 2.70 ± 0.52 |
| Neutrophils | % | 4.50 ± 0.97 | 2.58 ± 0.12 | 3.22 ± 0.33 | 3.08 ± 0.28 | 3.96 ± 1.21 |
| Eosinophils | % | 1.25 ± 0.22 | 0.92 ± 0.04 | 0.92 ± 0.15 | 0.85 ± 0.10 | 1.13 ± 0.21 |
| Basophils | % | 0.06 ± 0.02 | 0.06 ± 0.02 | 0.06 ± 0.02 | 0.06 ± 0.02 | 0.06 ± 0.02 |
| Clotting time | Seconds | 64.2 ± 19.90 | 33.0 ± 5.46 | 26.40 ± 3.09 | 39.00 ± 11.79 | 53.80 ± 14.61 |

Values are expressed as mean ± SEM (n = 10 for each group).
*$p < 0.05$ were considered significant using one-way ANOVA followed by Tukey's multiple comparison test.

TABLE 5

Effect of the composition on serum biochemical parameters in rats

| | | | Composition (mg/kg) | | | |
|---|---|---|---|---|---|---|
| | Unit | Control | 250 | 500 | 1,000 | 1,000 Reversal |
| Male | | | | | | |
| ALT | IU/L | 209.2 ± 69.38 | 212.0 ± 60.64 | 146.8 ± 7.14 | 219.0 ± 46.85 | 66.0 ± 6.88 |
| AST | IU/L | 296.9 ± 53.02 | 279.6 ± 43.44 | 228.6 ± 10.88 | 238.8 ± 25.25 | 208.4 ± 20.78 |
| ALP | IU/L | 276.9 ± 39.06 | 246.1 ± 5.54 | 221.4 ± 29.71 | 207.2 ± 18.54 | 299.3 ± 39.60 |
| Total Protein | g/dL | 6.20 ± 0.39 | 12.08 ± 3.37 | 8.0 ± 1.36 | 5.90 ± 1.33 | 8.52 ± 0.46 |
| Albumin | mg/dL | 3.60 ± 0.19 | 4.58 ± 0.76 | 5.24 ± 1.37 | 6.62 ± 1.59 | 4.06 ± 0.25 |
| Glucose | mg/dL | 115.7 ± 6.16 | 135.1 ± 7.95 | 92.22 ± 16.19 | 131.3 ± 19.92 | 114.9 ± 10.15 |
| Total bilirubin | mg/dL | 0.24 ± 0.24 | 0.24 ± 0.02 | 0.26 ± 0.04 | 0.74 ± 0.31 | 0.26 ± 0.024 |
| Direct bilirubin | mg/dL | 0.12 ± 0.02 | 0.10 ± 0.03 | 0.160 ± 0.04 | 0.14 ± 0.05 | 0.120 ± 0.02 |
| Urea | mg/dL | 37.43 ± 5.72 | 35.17 ± 3.32 | 33.83 ± 3.83 | 48.17 ± 4.30 | 54.67 ± 6.33 |
| Creatinine | mg/dL | 0.64 ± 0.07 | 0.79 ± 0.31 | 2.18 ± 1.14 | 1.74 ± 0.91 | 0.84 ± 0.05 |
| Cholesterol | mg/dL | 53.03 ± 7.22 | 57.13 ± 5.34 | 63.78 ± 2.80 | 58.57 ± 21.28 | 78.85 ± 6.40 |
| Triglycerides | mg/dL | 52.57 ± 14.57 | 51.34 ± 10.32 | 66.43 ± 9.29 | 58.75 ± 20.85 | 70.86 ± 6.37 |
| HDL | mg/dL | 43.08 ± 4.87 | 47.99 ± 3.80 | 50.11 ± 1.60 | 53.53 ± 6.99 | 68.72 ± 5.94** |
| Calcium | mg/dL | 9.87 ± 0.78 | 19.37 ± 9.54 | 12.60 ± 3.15 | 14.56 ± 4.40 | 10.96 ± 0.55 |
| Phosphorous | mg/dL | 17.32 ± 6.07 | 24.04 ± 6.85 | 22.38 ± 3.1 | 26.08 ± 11.58 | 21.34 ± 16.60 |
| Female | | | | | | |
| ALT | IU/L | 74.40 ± 4.88 | 105.0 ± 15.44 | 101.4 ± 10.46 | 108.6 ± 16.59 | 52.2 ± 7.14 |
| AST | IU/L | 170.6 ± 7.69 | 180.4 ± 15.46 | 178.5 ± 17.91 | 189.0 ± 23.67 | 175.5 ± 9.74 |
| ALP | IU/L | 160.0 ± 17.89 | 190.5 ± 31.15 | 142.7 ± 6.46 | 184.6 ± 34.12 | 165.4 ± 18.7 |
| Total Protein | g/dL | 13.90 ± 1.24 | 14.1 ± 1.56 | 11.48 ± 1.00 | 11.84 ± 1.59 | 10.58 ± 1.14 |
| Albumin | mg/dL | 4.08 ± 0.08 | 3.86 ± 0.09 | 3.720 ± 0.31 | 3.82 ± 0.198 | 3.66 ± 0.19 |
| Glucose | mg/dL | 107.7 ± 9.17 | 117.8 ± 22.54 | 121.1 ± 11.32 | 110.1 ± 34.12 | 109.9 ± 6.27 |
| Total bilirubin | mg/dL | 0.28 ± 0.04 | 0.34 ± 0.14 | 0.36 ± 0.09 | 0.26 ± 0.07 | 0.32 ± 0.037 |
| Direct bilirubin | mg/dL | 0.16 ± 0.02 | 0.18 ± 0.08 | 0.24 ± 0.05 | 0.14 ± 0.02 | 0.16 ± 0.02 |
| Urea | mg/dL | 123.2 ± 13.82 | 107.8 ± 17.75 | 150.7 ± 36.99 | 130.7 ± 12.54 | 51.49 ± 3.86 |
| Creatinine | mg/dL | 0.43 ± 0.04 | 1.09 ± 0.66 | 1.83 ± 1.21 | 1.04 ± 0.17 | 0.69 ± 0.1 |
| Cholesterol | mg/dL | 69.58 ± 8.39 | 55.86 ± 4.96 | 53.24 ± 6.20 | 63.03 ± 8.54 | 61.76 ± 3.76 |
| Triglycerides | mg/dL | 65.15 ± 12.15 | 44.65 ± 13.84 | 53.12 ± 10.79 | 44.05 ± 23.35 | 101.7 ± 29.26 |
| HDL | mg/dL | 64.70 ± 5.65 | 60.44 ± 5.52 | 62.44 ± 6.70 | 68.13 ± 3.76 | 74.76 ± 3.92 |
| Calcium | mg/dL | 9.41 ± 0.19 | 8.44 ± 0.42 | 9.54 ± 0.90 | 7.35 ± 2.65 | 9.33 ± 0.13 |
| Phosphorous | mg/dL | 23.02 ± 2.88 | 14.90 ± 5.17 | 13.28 ± 5.31 | 22.70 ± 6.80 | 24.42 ± 4.2 |

Values are expressed as mean ± SEM (n = 10 for each group).
*p < 0.05 were considered significant using one-way ANOVA followed by Tukey's multiple comparison test.

The histopathological examination of vital organs showed no toxic signs. The treatment with 1,000 mg/kg b.w. did not induce any change in the cellular architecture of the examined tissues of male or female rats.

The composition was evaluated for potential acute and sub-acute oral toxicity in experimental animals such as Wistar rats. Single dose 2,000 mg/kg body weight administration of the composition was found to be non-toxic in female rats. Further, 28-day repeated dose administration of the composition at the doses of 250, 500 and 1,000 mg/kg body weight resulted in no mortality, toxic clinical signs, or target organ toxicity in male or female Wistar rats. The No-Observable-Adverse-Effect-Level (NOAEL) of the composition was found to be 1,000 mg/kg body weight in rats.

Example 2—Effect of the Composition on Gastric Emptying and Gastrointestinal Transit Time in Sprague-Dawley Rats A composition of *asafoetida* and milk thistle extract in a ratio of 1:3 was evaluated for effects on gastric emptying and gastrointestinal transit is Sprague-Dawley rats. Twenty-four male Sprague Dawley (SD) rats (190-200 g) were divided into four groups, each group consisted of six animals with less than 20% mean body weight range. Group I served as control group, Group II referenced standard Domiperidone, Groups III and IV were administered the composition. During experimentation, animals were housed under standard husbandry conditions at a temperature of 22±3° C., relative humidity (30-70%) and a light:dark cycle of 12:12 h. Animals were allowed free access to pellet feed and UV purified water.

| Groups | Treatment mg/kg B.W (Orally) | No. of animals |
|---|---|---|
| I | Physiological saline 10 ml/kg | 6 |
| II | Domperidone 10 mg | 6 |
| III | Composition 50 mg | 6 |
| IV | Composition 100 mg | 6 |

All treatments were given for seven days daily in the morning except reference standard and on day $8^{th}$ after fasted for 16 h all groups were administered with respective doses of the composition or standard drug Domperidone. Gastric emptying was measured by the use of phenol red method as described previously (Kawachi et al. 2011). Post 1 h administration of the composition or Domperidone, the animals were administered intragastrically with 1.5% carboxymethyl cellulose sodium salt containing 0.05% phenol red. Rats were sacrificed after 20 minutes. Stomachs were harvested, and gastric content collected. The gastric content was treated with 10 mL of 0.1 M $NaHCO_3$ and centrifuged at 3,000 rpm for 15 minutes. The amount of phenol red in the supernatant was determined based on the absorbance at 570 nm measured using a microplate reader (Multiskan EX, Thermo Scientific). The amount of phenol red from an animal sacrificed immediately after the above-mentioned administration procedure was used as the standard sample. Gastric emptying was calculated using the formula: (1−amount of phenol red in the test sample/amount of phenol red in the standard sample)×100.

Body weights of each animal group were measured at initiation of experiment, on day 7, and fasting on day 8. Mean body weight of all groups measured at time of randomization, on day 7 and fasting body weight on day 8, revealed no significant change (Table 6).

TABLE 6

Effect of the composition administration on body weight in rats

| Group | Body weight (g) | | |
|---|---|---|---|
| | Initial | Day 7 | Fasting (Day 8) |
| Control | 201.69 ± 9.02 | 217.44 ± 9.69 | 203.54 ± 9.27 |
| Domiperidone 10 mg/kg | 209.68 ± 9.71 | 228.69 ± 12.07 | 211.9 ± 11.72 |
| Composition 50 mg/kg | 200.17 ± 6.97 | 224.16 ± 13.91 | 208.23 ± 12.37 |
| Composition 100 mg/kg | 210.64 ± 10.4 | 224.32 ± 10.79 | 210.63 ± 10.27 |

Values are expressed as Mean ± SEM; n = 6.
Data were analyzed by one-way ANOVA followed by Dunnet's t test.
*p < 0.05 compared to control group.

The percentage gastric emptying was assessed after 20 minutes of phenol red meal administration in rats. The gastric emptying was lower in control animals (64.94%) while the animals in the Domperidone treated group showed an increase in percentage of gastric emptying (78.86%). Rats treated with 50 mg/kg and 100 mg/kg doses of the composition exhibited increased percentage of gastric emptying (69.8% and 74.79% respectively) as compared to control.

Further, in the present study gastrointestinal transit (GIT) was found to be increasing significantly in the extract and standard drug treated rats as compared to control. The GIT was 55.19% in control group. There was a significant increase in GIT among the animals treated with single dose of Domperidone (p<0.001). Composition-administered rats showed significant improvement in the GIT dose dependently (p<0.001). The percentage GIT was 68.9 and 70.28 respectively for 50 mg/kg and 100 mg/kg composition.

The composition in beadlet form was evaluated for efficacy in alleviating the delayed gastric emptying using an animal model. The effect of 7-day administration of the composition at 50 and 100 mg/kg body weight in male Sprague-Dawley rats (190-200 g), on gastric emptying and gastrointestinal transit time was evaluated using phenol red method. Composition treatment increased the gastric emptying in rats, comparable to the standard drug Domperidone (10 mg/kg body weight). Further, the composition significantly improved the gastrointestinal transit time in rats.

Example 3—Safety and Efficacy of the Composition in Human Subjects with Non-Ulcer Functional Dyspepsia A composition of *asafoetida* and milk thistle extract in a ratio of 1:3 was evaluated for the treatment of established symptoms of functional dyspepsia in human subjects.
Participants—Eligibility Criteria
Adult male and female volunteers aged 18-60 years presenting symptoms of dyspepsia (Rome III diagnostic criteria for functional dyspepsia) were recruited. Subjects with history of psychiatric illness, congestive heart failure or uncontrolled hypertension, peptic ulcers, gastro oesophageal reflux disease, gastrointestinal surgery or any other clinically significant gastrointestinal disease, gastrointestinal bleeding, mechanical obstruction, perforation, or gastrointestinal cancer were excluded from the study. Other exclusion criteria were pregnant or lactating women. Further, subjects unwilling/unable to comply with the protocol requirements were excluded from the study.
Interventions The active treatment contained 250 mg of a 1:3 blend of *asafoetida* (oleo-gum resin) and milk thistle extract respectively. The formulation was prepared by mixing 100 mg of *asafoetida* (oleo-gum resin) and 300 mg of milk thistle extract. Composition capsules contained 250 mg of the blended active ingredients (Table 7).

TABLE 7

Details of investigational products/treatments

| Product | Composition | Placebo |
|---|---|---|
| Active ingredient | 1:3 blend of *F. asafoetida* extract and *S. marianum* (milk thistle) extract | Maltodextrin |
| Dosage Form | Capsules | Capsules |
| Route | Oral | Oral |
| Dose | 250 mg (active Ingredient) twice a day | 400 mg twice a day |
| Dosing Regimen | Twice a day after food | Twice a day after food |
| Treatment duration | 7 days | 7 days |
| Manufacturer | Vidya Herbs (P) Ltd. | Vidya Herbs (P) Ltd. |
| Batch/Lot No. | VH/ASM/F17749 | VH/ASM/F17749 |
| Manufacture Date | March 2018 | March 2018 |
| Expiration Date | February 2021 | February 2021 |

During the 7-day treatment period, the daily oral intake was two capsules containing either placebo (maltodextrin) or composition (=500 mg/day). All capsules were of the same appearance, color and odor. The subjects had to record their daily food consumption during the intervention period to ensure that there was no change in the dietary habits throughout study period.
Trial Design This was a randomized, double blind, placebo controlled, parallel group, single center study performed on seventy human volunteers. This study was conducted in compliance with the protocol, International Conference on Harmonization (ICH) Good Clinical Practice (GCP) Guidelines, including ICH E6, and applicable local regulatory requirements and laws. This clinical trial adhered to the CONSORT guidelines. The information on the nature, purpose, and risks of the study were provided to each subject or subject's legally authorized representative before their participation. Written informed consent for participation and publication of the data was obtained prior to the subjects entering the study (before initiation of protocol-specified procedures). After passing the eligibility criteria, subjects were randomized to two intervention groups: composition and placebo in 50:50 ratio (capsule form, 500 mg/day). The subjects arrived at the site in the fasted state and blood samples were collected for laboratory assessment. Post blood sample collection, dyspepsia was assessed with gastrointestinal symptom rating scale (GSRS) scoring, Glasgow dyspepsia severity score (GDSS) and Short Form of Nepean Dyspepsia index (NDI-SF) questionnaire as planned in the study.

Efficacy End Points

The efficacy endpoint for the study was response to treatment at Day 7 (Visit 2).

Response was defined as the

- Changes in Gastrointestinal Symptom Scale score from baseline to end of the study
- Changes in Glasgow Dyspepsia Severity score from baseline to end of the study
- Changes in Nepean Dyspepsia Index from base line to end of the study Comparison of the means scores between baseline and end of study is done using paired sample t-test with 5% level of significance. Comparison within treatment groups was done using independent sample t-test by considering the change in baseline and the end of the study.

The safety evaluation was based on physical examination, vital signs (blood pressure [systolic and diastolic], heart rate, respiratory rate, and temperature), clinical laboratory tests (hematology, clinical chemistry), and adverse events (AEs).

Statistical Analysis

Statistical analyses were performed after all subjects had ended their participation in the study and the database was locked.

Categorical variables were summarized using frequencies and percentages.

Percentages were presented to two decimal places. All percentages >0% and <0.1%, were presented as "<0.1%" instead of actual calculated percentages against the respective counts in tables.

Continuous variables were summarized using descriptive statistics (number of subjects with an observation [N], mean, standard deviation [SD], median, minimum [min] and maximum [max]).

Study Outcomes

Overall 78 subjects were screened and 8 were screen failures in the study. A total of 70 subjects were randomized in the study with 35 each in the composition and placebo groups. All 70 subjects were included in the analysis.

The baseline demographics of all the participants are presented in Tables 8A and 8B. Overall, the majority of the subjects were male (57.14%) with 68.57% in the composition group. The mean age of subjects enrolled in the study was 37.93±11.79 years with minimum age of 20 years and maximum age of 60 years. The subjects had mean height of 163.69±6.30 cm, mean weight of 59.04±9.40 kg, and a BMI of 22.04±3.43 kg/m². All subjects in the study were of Indian origin.

The demographic characteristics in terms of age, height, weight and BMI were comparable between the study groups.

TABLE 8A

Demographic characteristics (Gender) of subjects enrolled in the study

| Gender | Composition | | Placebo (n = 35) | | All (n = 70) | | p† |
|---|---|---|---|---|---|---|---|
| | n | % | n | % | n | % | |
| Male | 24 | 68.57 | 16 | 45.71 | 40 | 57.14 | 0.0533 |

†Pearson's Chi-square test

TABLE 8B

Demographic characteristics (age, height, weight and BMI) of subjects enrolled in the study

| | Composition (N = 35) | Placebo (N = 35) | All (N = 70) | p† |
|---|---|---|---|---|
| Age (Years) | | | | |
| Mean | 40.37 | 35.49 | 37.93 | 0.0830 |
| SD | 11.47 | 11.77 | 11.79 | |
| Minimum | 23 | 20 | 20 | |
| Median | 39 | 32 | 35 | |
| Maximum | 60 | 59 | 60 | |
| Height (cm) | | | | |
| Mean | 164.9 | 162.5 | 163.69 | |
| SD | 6.67 | 5.74 | 6.3 | 0.1019 |
| Minimum | 150 | 152 | 150 | |
| Median | 167.00 | 163.00 | 164.50 | |
| Maximum | 176 | 172 | 176 | |
| Weight (kg) | | | | |
| Mean | 61.34 | 56.74 | 59.04 | 0.0396 |
| SD | 9.06 | 9.29 | 9.4 | |
| Minimum | 45 | 42 | 42 | |
| Median | 63 | 56 | 59 | |
| Maximum | 80 | 77 | 80 | |
| BMI (kg/m²) | | | | |
| Mean | 22.63 | 21.46 | 22.04 | 0.157 |
| SD | 3.7 | 3.08 | 3.43 | |
| Minimum | 16.53 | 15.79 | 15.79 | |
| Median | 22.23 | 20.83 | 22.01 | |
| Maximum | 34.01 | 26.96 | 34.01 | |

N: No of subjects;
SD: Standard deviation:
BMI: Body Mass Index

Efficacy Evaluation—Primary End Point Analysis

Gastrointestinal Symptom Scale (GSRS) Score:

The GSRS is a Swedish, disease-specific and self-administered questionnaire, designed to evaluate perceived severity of gastrointestinal symptoms during the previous week. The questionnaires included 15 items and used a 7-grade Likert scale. The items were divided into five dimensions representing reflux syndrome (two items), abdominal pain syndrome (three items), constipation syndrome (three items), indigestion syndrome (four items) and diarrhea syndrome (three items) (Roth and Ohlsson, 2013).

Summary of mean score for symptom severity on GSRS scoring by visit and treatment is presented in Table 9. There was a significant decrease (p<0.001) of GSRS score noted in the composition group (from 32.11±8.6 at baseline to 19.11±5.4 EOS). A highly significant (p<0.001) mean change from baseline in the GSRS score was observed in the composition group (13.0±8.3) compared to placebo group (2.0±2.7) at the end of the study.

Analysis of individual dyspepsia symptoms on GSRS scoring showed marked improvement in the heartburn, rumbling, burping, passing gas or flatus symptoms in the subjects of the composition group at the end of study compared to the baseline.

TABLE 9

Mean score for symptom severity on Gastrointestinal Symptom Rating Scale (GSRS)

| Visit | Group A (Composition) | | | | Group B (Placebo) | | | | p-value (between groups) |
|---|---|---|---|---|---|---|---|---|---|
| | N | Mean ± SD | Median | Min, Max | N | Mean ± SD | Median | Min, Max | |
| Visit_1 | 35 | 32.11 ± 8.6 | 33 | 3, 46 | 35 | 25.23 ± 3.6 | 26 | 18, 35 | <0.001‡** |
| Visit_2 | 35 | 19.11 ± 5.4 | 19 | 1, 28 | 35 | 23.2 ± 4.9 | 22 | 15, 35 | 0.0014‡* |
| Change | 35 | 13.0 ± 8.3 | 14 | −16, 26 | 35 | 2.0 ± 2.7 | 1 | −4, 11 | <0.001‡** |
| p-value (visit_1 vs. visit_2) | | <0.001#** | | | | <0.001#** | | | |

Change = Visit_1 − Visit_2
Paired t-test (Visit_1 vs Visit_2)
‡Independent t-test
*p < 0.01 and
**p < 0.001

Glasgow Dyspepsia Severity Score (GDSS):

Glasgow dyspepsia severity score (GDSS) is a validated multidimensional disease specific scale for dyspepsia. It focuses on several aspects of dyspepsia: firstly, the frequency of dyspepsia symptoms and the effect that they have on normal activities and ability to work; secondly, the need for consultations with physicians for dyspepsia and the need for diagnostic investigations for dyspepsia; and thirdly, the need for over-the-counter and prescription medication for dyspepsia (el-Omar et al. 1996).

Summary of mean score for symptom severity on GDSS scoring by visit and treatment is presented in Table 10.

Compared to the baseline a significant reduction (p<0.001) of GDSS questionnaire score was noted in the composition group (from 5.66±3.1 to 5.09±2.8) compared to placebo group (from 2.77±1.3 to 2.69±1.3) at the end of the study.

A significant (p<0.05) mean change from baseline in the GDSS questionnaire score was observed in the composition group (0.57±1.7) compared to placebo group (0.08±0.4) at the end of the study.

Compared to the baseline a significant reduction ((p<0.001) of NDI-SF scoring was noted in the composition group (from 15.74±4.1 to 11.54±2.1) compared to placebo group (from 12.54±3.2 to 11.63±2.6) at the end of the study.

A significant (p<0.001) mean change from baseline in the NDI-SF scoring was observed in the composition group (4.2±4.08) compared to placebo group (0.91±2.2) at the end of the study.

Analysis of individual domains of NDI-SF quality of life aspects showed marked improvement in tension, interference with daily activities and eating/drinking in the subjects of the composition group at the end of study compared to the baseline.

Adverse Events

No adverse or serious adverse events were evident throughout the study period.

7-day treatment with 500 mg/day of the composition significantly alleviated the symptoms of dyspepsia, improving the quality of life. Composition treatment did not induce any toxicity as no adverse events were observed during or after the study period.

TABLE 10

Mean Score for Symptom Severity on Glasgow Dyspepsia Severity Score (GDSS)

| Visit | Group A (Composition) | | | | Group B (Placebo) | | | | p-value (between groups) |
|---|---|---|---|---|---|---|---|---|---|
| | N | Mean ± SD | Median | Min, Max | N | Mean ± SD | Median | Min, Max | |
| Visit_1 | 35 | 5.66 ± 3.1 | 4 | 2, 14 | 35 | 2.77 ± 1.3 | 3 | 0, 6 | <0.001‡** |
| Visit_2 | 35 | 5.09 ± 2.8 | 4 | 1, 10 | 35 | 2.69 ± 1.3 | 3 | 0, 6 | <0.001‡** |
| Change | 35 | 0.57 ± 1.7 | 0 | −1, 8 | 35 | 0.08 ± 0.4 | 0 | −1, 1 | 0.06‡ |
| p-value (visit_1 vs. visit_2) | | <0.027#* | | | | 0.183# | | | |

Change = Visit_1 − Visit_2
Paired t-test (Visit_1 vs Visit_2)
‡Independent t-test
*p < 0.01 and
**p < 0.001

Nepean Dyspepsia Index:

The short form of Nepean Dyspepsia Index (NDI-SF) is reliable and valid measure of quality of life in non-ulcer functional dyspepsia. NDI-SF consists of 10 questions with 5 domains (tension, interference with daily activity, eating/drinking, knowledge/control, work/study) (Talley et al. 2001).

REFERENCES

Aro P, Talley N J, Ronkainen J, Storskrubb T, Vieth M, Johansson S E et al. Anxiety is associated with uninvestigated and functional dyspepsia (Rome III criteria) in a Swedish population-based study. Gastroenterol 2009; 137: 94-100

Choung R S, Locke G R, Schleck C D, Zinsmeister A R, Talley N J. Do distinct dyspepsia subgroups exist in the community? A population-based study. Am J Gastroenterol 2007; 102:1983-1989

Duan H, Takaishi Y, Tori M, Takaoka S, Honda G, Ito M, et al. Polysulfide derivatives from *Ferulafoetida*. J Nat Prod 2002; 65:1667-1669 el-Omar E M, Banerjee S, Wirz A, McColl K E. The Glasgow Dyspepsia Severity Score—a tool for the global measurement of dyspepsia. Eur J Gastroenterol Hepatol 1996; 8(10):967-71.

Kawachi M, Matsunaga Y, Tanaka T, Hori Y, Ito K, Nagahama K et al. Acotiamide hydrochloride (Z-338) enhances gastric motility and emptying by inhibiting acetylcholinesteraseactivity in rats. Eur J Pharmacol 2011; 666: 218-225.

Khazim K, Gorin Y, Cavaglieri R C, Abboud H E, Fanti P. The antioxidant silybin prevents high glucose-induced oxidative stress and podocyte injury in vitro and in vivo. American J Physiol Renal Physiol 2013; 305 (5):F691-F700.

Lahner E, Bellentani S, Bastiani R D et al. A survey of pharmacological and nonpharmacological treatment of functional gastrointestinal disorders. United European Gastroenterol J 2013; 1(5): 385-393.

Mahendra P, Bisht S. *Ferula asafoetida*: traditional uses and pharmacological activity. Pharmacogn Rev 2012; 6:141-146

Monkemuller K, Malfertheiner P. Drug treatment of functional dyspepsia. World J Gastroenterol 2006; 12(17): 2694-700

Natural Medicines Comprehensive Database: professional version. Milk Thistle monograph. Stockton (CA): Therapeutic Research Faculty. 2012.

Roth B, Ohlsson B. Gastrointestinal symptoms and psychological well-being in patients with microscopic colitis. Scand J Gastroenterol 2013; 48(1): 27-34.

Sahebkar A, Iranshahi M. Biological activities of essential oils from the genus *Ferula* (Apiaceae). Asian Biomed 2010; 4:835-847

Sewell R D E, Rafieian-kopaei M. The history and ups and downs of herbal medicines usage. J Herbmed Pharmacol 2014; 3(1):1-3

Simanek V, Kren V, Ulrichova J, Vicar J, Cvak L. Silymarin—What is in the name? Hepatology 2000; 32:442-443

Takeoka G. Volatile constituents of *Asafoetida*. In: Takeoka G R, Guntert M, Engel K-H, editors. Aroma active compounds in foods. Washington, D.C.: American Chemical Society; 2001, p. 33-44.

Talley N J, Verlinden M, Jones M. Quality of life in functional dyspepsia: responsiveness of the Nepean Dyspepsia Index and development of a new 10-item short form. Aliment PharmacolTher. 2001; 15(2): 207-16.

Talley N J. *Helicobacter pylori* and dyspepsia. Yale J Biol Med. 1999 March-June; 72(2-3):145-51.

The invention claimed is:

1. A composition for promoting digestive health, comprising an effective amount of an extract of Ferula asafoetida and an effective amount of an extract of *Silybum marianum* containing at least 25% silymarin, wherein said extract of *Ferula asafoetida* and said extract of Silybum marianum are present in a ratio of about 1:3, respectively.

2. The composition of claim 1, wherein said extract of *Ferula asafoetida* comprises oleoresin.

3. The composition of claim 1, wherein said composition is in a form selected from the group consisting of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, sol, injection, and combinations thereof.

4. The composition of claim 1, wherein said composition further comprises at least one of a vitamin, mineral, extract, amino acid, protein, carbohydrate, lipid, fatty acid, food, beverage, nutritional supplement, dietary supplement, excipient, pharmaceutically acceptable carrier, bulking agent, binding agent, caffeine, flavoring, sweetener, and preservative.

5. The composition of claim 1, wherein said extract of *Ferula asafoetida* and said extract of *Silybum marianum* have a total combined dose of between about 250 mg and about 500 mg.

6. The composition of claim 1, wherein said composition further comprises a controlled-release formulation.

7. The composition of claim 6, wherein said controlled-release formulation is selected from an osmotic membrane, a polymer and a glycolipid.

8. The composition of claim 7, wherein said polymer is a swellable polymer or an acrylic polymer.

9. The composition of claim 7, wherein said polymer is a polymeric matrix.

10. The composition of claim 9, wherein said polymeric matrix is selected from poly-d,l-lactic acid, poly-L-lactic acid, polyglycolic acid, copolymers of mixed d,l-lactic acid and glycolic acid, copolymers of L-lactic acid and glycolic acid, copolyoxalates, polycaprolactone, poly (lactic acid-caprolactone), poly(glycolic acid-caprolactone), casein and albumin.

* * * * *